(12) United States Patent
Mulani

(10) Patent No.: US 7,841,751 B2
(45) Date of Patent: Nov. 30, 2010

(54) PEDIATRIC ADAPTER FOR TRANSILLUMINATION

(76) Inventor: Nizar A. Mulani, 719 Santa Maria, Sugar Land, TX (US) 77478

( * ) Notice: Subject to any disclaimer, the term of this patent is extended or adjusted under 35 U.S.C. 154(b) by 654 days.

(21) Appl. No.: 11/790,731

(22) Filed: Apr. 27, 2007

(65) Prior Publication Data
US 2008/0015663 A1    Jan. 17, 2008

Related U.S. Application Data

(60) Provisional application No. 60/795,558, filed on Apr. 28, 2006.

(51) Int. Cl.
*F21V 8/00*    (2006.01)
(52) U.S. Cl. .................. 362/362; 362/572; 362/249.02
(58) Field of Classification Search .......... 362/362, 362/572, 581, 555, 103, 249.01, 249.02, 362/368, 573, 574, 575; 356/369, 121–123; 600/247–249; 607/90, 88
See application file for complete search history.

(56) References Cited

U.S. PATENT DOCUMENTS

| | | | |
|---|---|---|---|
| 5,788,518 A | 8/1998 | Wachter et al. | |
| 6,280,032 B1 | 8/2001 | Kolta | |
| 6,830,547 B2 * | 12/2004 | Weiss | 600/221 |
| 7,006,223 B2 | 2/2006 | Mullani | |
| 2004/0201846 A1 * | 10/2004 | Mullani | 356/369 |

FOREIGN PATENT DOCUMENTS

EP    0 672 379    9/1995

OTHER PUBLICATIONS

Journal of Emergency Medical Services, vol. 30, No. 10, pp. 90, Oct. 2005, "No More Stab-in-the-Dark IV Sticks," Jeffrey Lindsey.

* cited by examiner

*Primary Examiner*—Sharon E Payne
(74) *Attorney, Agent, or Firm*—Welsh Flaxman & Gitler LLC

(57) ABSTRACT

A transillumination device can use an adapter to make it more appropriate for neonatal and pediatric application. The adapter attaches to the bottom of the transillumination device and covers the illumination source. An aperture in the adapter allows part of the light generated by the illumination source through the adapter and blocks the remaining light. The reduces light enhances the transillumination device's ability for viewing pediatric patients.

8 Claims, 3 Drawing Sheets

PEDIATRIC ADAPTER FOR TRANSILLUMINATION

This application claims the benefit of provisional application 60/795,558, filed Apr. 28, 2006.

BACKGROUND OF THE INVENTION

Transillumination entails shining of a light through a body cavity or organ for diagnostic purposes. Typically, transillumination is performed in a room where the lights have been dimmed or turned off to facilitate the viewing of the part being studied. A bright light is pointed at the cavity or organ and due to the slight translucence of the part under consideration, some light passes through the part. This test is often performed on newborns or infants with hydrocephalus or males suspected of having hydrocele. In addition, tests performed on breast tissue detect lesions and/or cysts. In newborns, the test is used to transilluminate the chest cavity if pneumothorax is suspected. Only in newborns is transillumination of the chest possible. Transillumination is painless and quickly performed with inexpensive equipment.

The classic mode of transillumination shines light in order to see internal details of the object. Another form of transillumination is side transillumination. In side transillumination, light shines from the side of the object to form a virtual light source below the skin. The light source moves with the device and allows transillumination of any part of the body up to a depth of about 6 mm.

When performing side transillumination, it is beneficial to shield the area to be viewed from ambient light. Side transillumination devices for neonatal applications generate too much light to be optimal.

It is an object of the invention to provide a device to perform transillumination on pediatric patients.

It is another object of the invention to provide an adapter for a transillumination device for use with a pediatric patient.

These and other objects of the invention will be apparent to one of ordinary skill in the art after reading the disclosure of the invention.

SUMMARY OF THE INVENTION

A transillumination device can use an adapter to make it more appropriate for neonatal and pediatric application. The adapter attaches to the bottom of the transillumination device and covers the illumination source. An aperture in the adapter allows part of the light generated by the illumination source through the adapter and blocks the remaining light. The reduced light enhances the transillumination device's ability for viewing pediatric patients.

DETAILED DESCRIPTION OF THE INVENTION

Figure 1:
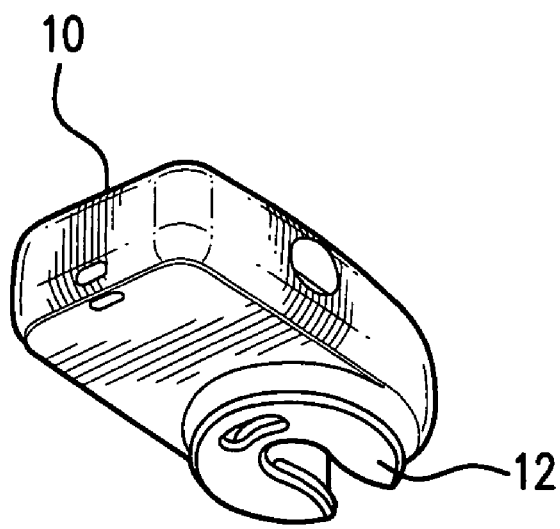
FIG. 1 is a bottom perspective view of a transillumination device having the pediatric adapter.

FIG. 1 shows the bottom view of the transillumination device 10 having the pediatric adapter 12. The manner in which the adapter functions and its attachment to the transillumination device will be explained in more detail below.

Figure 2:
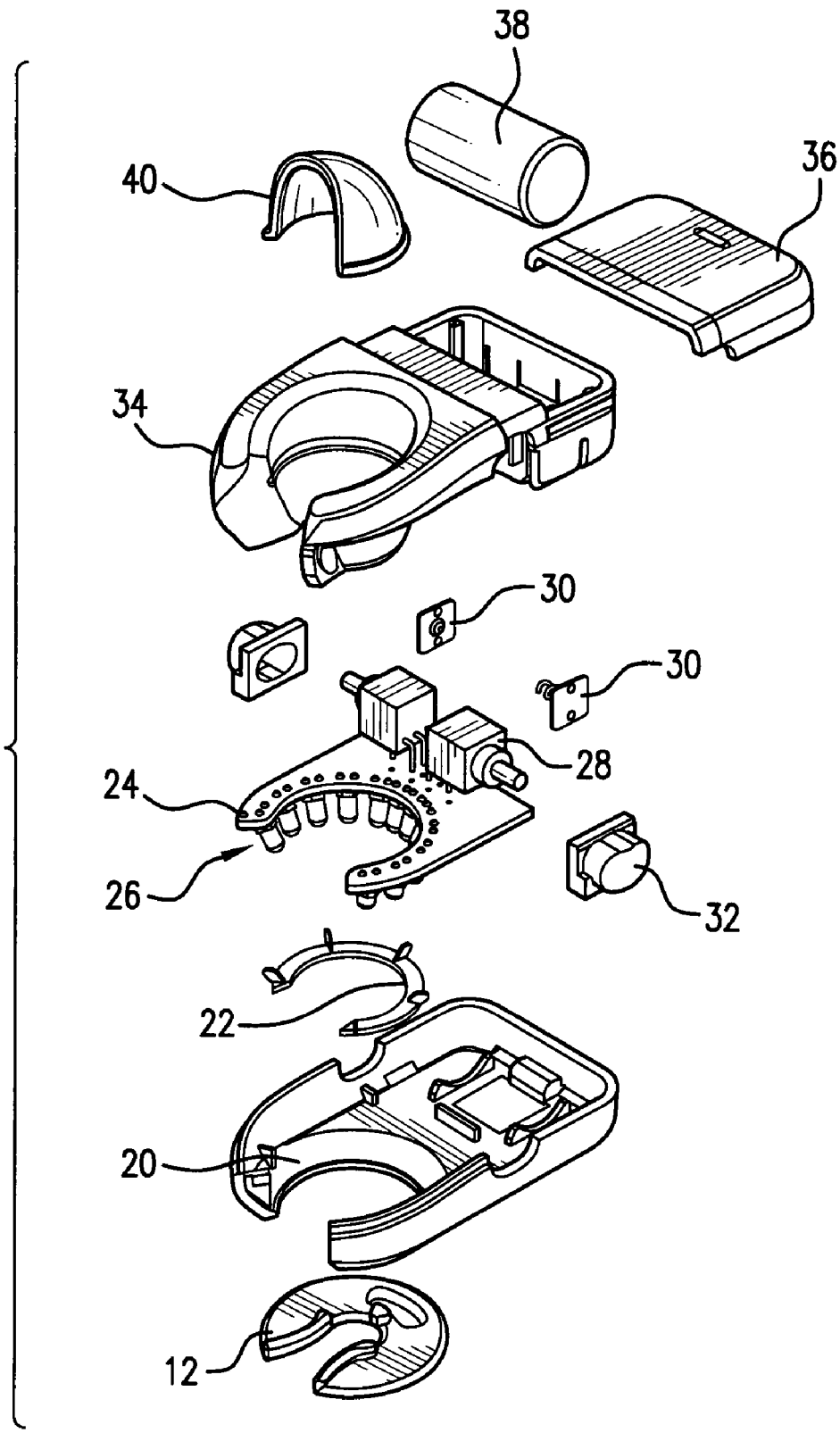
FIG. 2 is an exploded view of the transillumination device having the pediatric adapter.

FIG. 2 is an exploded view of the transillumination device and pediatric adapter. The adapter 12 attaches to the bottom 20 of the device. The bottom has an arcuate opening extending to the front edge to provide the user with a viewing area. A glass ring 22 extends about the edge of the opening. The device houses an illumination source, such as a printed circuit board 24 provided with LEDs 26. The user controls the illumination via a pair of actuators 28 and contact 30 extending between buttons 32 and the printed circuit board.

A top 34 and battery cover 36 complete the housing of the transillumination device. Like the bottom, the top 34 has an opening extending to the front edge to complete the viewing area. A battery 38 provides a source of power for the illumination source. A shield 40 helps block ambient light to improve the viewing of the target area by the user.

Figure 3:
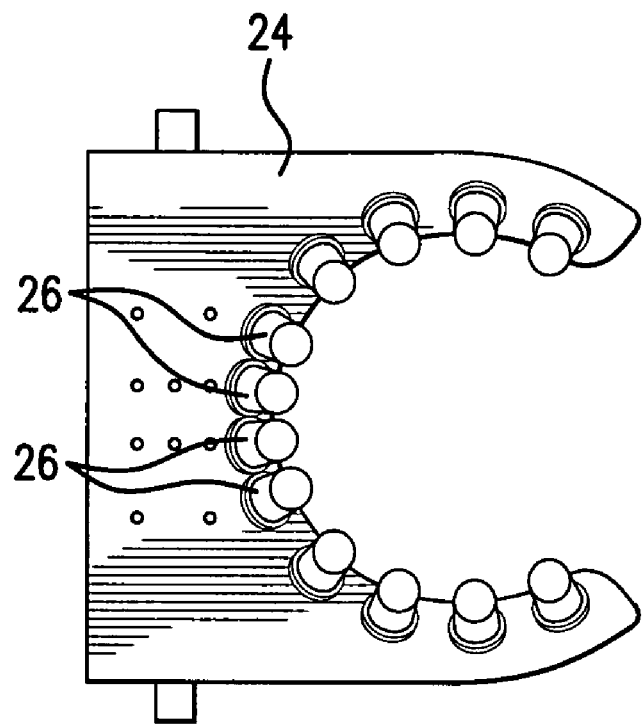
FIG. 3 is a bottom view of the illumination source of the transillumination device.

FIG. 3 shows a printed circuit board 24 having a series of twelve LEDs 26. The LEDS may be white, red or orange. The four LEDs in the middle are situated closer to one another than the remaining eight LEDs. The remaining eight LEDs are evenly distributed between the four central LEDS and the end of the arcuate opening formed in the printed circuit board.

Figure 4:
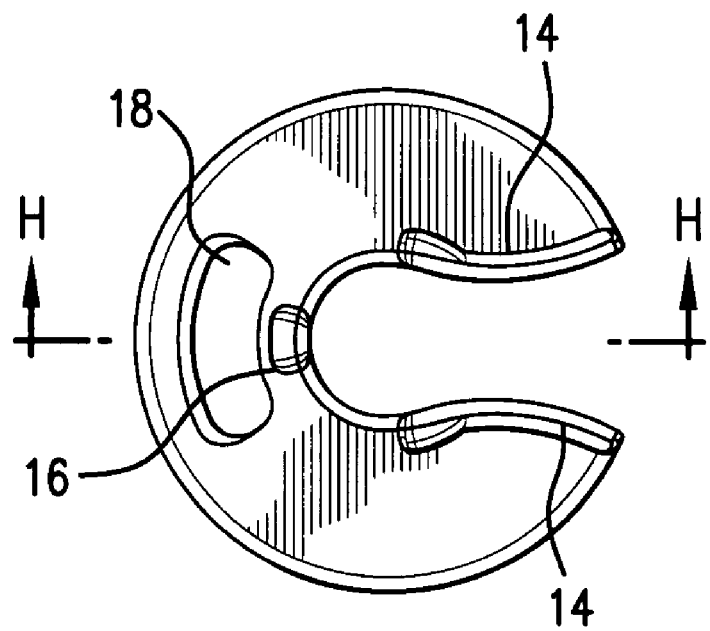
FIG. 4 is a top view of the pediatric adapter.

FIG. 4 depicts the top view of the adapter. The shape of the adapter corresponds to the openings in both the printed circuit board and transillumination device through which the user views the area being transilluminated. The adapter may be secured to the transillumination device in any suitable manner, including both removably or permanently. One such manner is the use of projection extending upwards from the top surface. The projections 14,16 releasably secure the adapter to the device by engaging the edge of the opening forming the viewing area.

An aperture 18 is formed in the adapter. When the adapter is attached to a transillumination device, the four central LEDs transmit light through the aperture 18. Light transmitted by the remaining LEDs is blocked by the adapter. The reduced transmitted light is advantageous for neonatal and pediatric applications.

Figure 5:
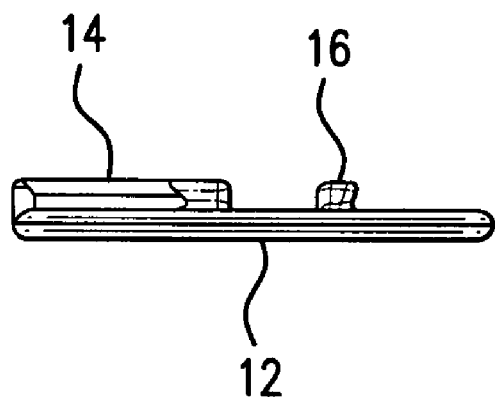
FIG. 5 is a side view of the pediatric adapter.

The side view of the adapter, seen in FIG. 5 clearly shows the extent of the projections 14,16 and their relationship to the rest of the adapter.

While the invention has been described with reference to preferred embodiments, variations and modifications would be apparent to one of ordinary skill in the art. The invention encompasses such variations and modifications.

I claim:

1. A transillumination device comprising
   a housing,
   a viewing area,
   a light source illuminating the viewing area, the light source including a first plurality of LEDs, a second plur and a third plurality of LEDs situated between said first and second plurality of LEDs,
   an adapter attached to the housing of the transillumination device and covering the light source, the adapter blocking part of the light emitted by the light source,
   wherein the adapter is arcuate and has a first and second end, and
   an aperture in the adapter allowing the passage of light produced by the third plurality of LEDs to be transmitted by the transillumination device, and further wherein the light produced by said first and second plurality of LEDs is blocked.

2. The device of claim 1, wherein
   the adapter is removably attached to the housing.

3. The device of claim 1, wherein
the aperture is spaced equidistantly from the first and second ends of the adapter.

4. The device of claim 1, further comprising
projections on the adapter engaging the housing.

5. The device of claim 1, further comprising
an aperture in the adapter allowing for the passage of flight.

6. An adapter for a transillumination device including a light source provided with a first plurality of LEDs, a second plurality of LEDs and a third plurality of LEDs situated between said first and second plurality of LEDs, the adapter comprising
an arcuate body having two ends,
an aperture within the body, and
means for removably connecting the arcuate body to a transillumination device;
wherein the aperture is equidistant from the two ends of the arcuate body, and further the aperture permits light produced by the third plurality of LEDs to be transmitted through the aperture and the light produced by said first and second plurality of LEDs to be blocked by the adapter.

7. The adapter of claim 6 wherein the means for connection comprise projections.

8. The transillumination device in accordance with claim 1, wherein the distance between each of the LEDs of the third plurality of LEDs is less than the distance between each of the LEDs of the first and second plurality of LEDs.

* * * * *

UNITED STATES PATENT AND TRADEMARK OFFICE
CERTIFICATE OF CORRECTION

| | | |
|---|---|---|
| PATENT NO. | : 7,841,751 B2 | Page 1 of 1 |
| APPLICATION NO. | : 11/790731 | |
| DATED | : November 30, 2010 | |
| INVENTOR(S) | : Nizar A. Mulani | |

It is certified that error appears in the above-identified patent and that said Letters Patent is hereby corrected as shown below:

Column 2, line 48, cancel the text beginning with "1. A transillumination device" to and ending "is blocked." in column 2, line 65, and insert the following claim:

--1. A transillumination device comprising
a housing,
a viewing area,
a light source illuminating the viewing area, the light source including a first plurality of LEDs, a second plurality of LEDs, and a third plurality of LEDs situated between said first and second plurality of LEDs,
an adapter attached to the housing of the transillumination device and covering the light source, the adapter blocking part of the light emitted by the light source,
wherein the adapter is arcuate and has a first and second end, and
an aperture in the adapter allowing the passage of light produced by the third plurality of LEDs to be transmitted by the transillumination device, and further wherein the light produced by said first and second plurality of LEDs is blocked.

Signed and Sealed this
Fourteenth Day of June, 2011

David J. Kappos
*Director of the United States Patent and Trademark Office*